United States Patent [19]

Saiki et al.

[11] Patent Number: 5,236,903
[45] Date of Patent: Aug. 17, 1993

[54] POLYPEPTIDE COMPRISING REPEATED CELL-ADHESIVE CORE SEQUENCES

[75] Inventors: Ikuo Saiki, Hokkaido; Norio Nishi, Hokkaido; Ichiro Azuma, 3-2, Makomanai Kami-cho 5-chome, Minami-ku, Sapporo-shi, Hokkaido; Seiichi Tokura, Hokkaido, all of Japan

[73] Assignee: Ichiro Azuma, Sapporo, Japan

[21] Appl. No.: 912,323

[22] Filed: Jul. 13, 1992

Related U.S. Application Data

[62] Division of Ser. No. 370,182, Jun. 23, 1992, Pat. No. 5,183,804.

[30] Foreign Application Priority Data

Jun. 24, 1988 [JP] Japan .................... 63-156133

[51] Int. Cl.$^5$ .......................... C07K 7/06; C07K 7/08; C07K 7/10; A61K 37/02
[52] U.S. Cl. ........................ 514/12; 514/13; 514/14; 514/15; 530/324; 530/325; 530/326; 530/327; 530/328; 930/DIG. 800
[58] Field of Search ............. 514/12, 18; 530/324, 530/325, 326, 327, 328, 329

[56] References Cited

U.S. PATENT DOCUMENTS

| | | | |
|---|---|---|---|
| 4,929,601 | 5/1990 | Brunetto et al. | 514/18 |
| 4,988,621 | 1/1991 | Ruoslahti et al. | 435/240.2 |
| 5,041,380 | 8/1991 | Ruoslahti et al. | 435/240.2 |

OTHER PUBLICATIONS

Humphries et al, *Science*, vol. 23, Jul. 25, 1986, pp. 467-470, "A Synthetic Peptide from Fibronectin Inhibits Experimental Metastasis of Murine Melanoma Cells".
Iwamoto et al, *Science*, vol. 238, Nov. 20, 1987, pp. 1132-1134, "YIGSR, a Synthetic Laminin Pentapeptide, Inhibits Experimental Metastasis Formation".
Saiki et al, *British Journal of Cancer*, vol. 59, No. 2, Feb. 1989, pp. 194-197, "The Inhibition of Murine Lung Metastasis by Synthetic Polypeptides . . . ".
EMBO Journal, vol. 4, 1985, pp. 2519-2524, IRL Press Ltd., Oxford, Great Britain, S. Suzuki et al, "Complete amino acid sequence of human vitronectin deduced from cDNA. Similarity of cell attachment sites in vitro-nectin and fibronectin".
Partial European Search Report of EP 89 11 1468, Nov. 26, 1990.
Kunitake et al., *Adv. Polymer Sci.*, 20: 159-211, 1976.
Nishi et al., *Int. J. Peptide Protein Res.*, 30: 275-283, 1987.
Saiki, I. et al., *Cancer Research*, 49, 3815-3822, Jul. 15, 1989.
Ruoslahti et al. Science 238 491 (1987) [Oct. 23].
Tressler et al. Cancer Communications 01 (1989) 55-63.

*Primary Examiner*—Merrell C. Cashion, Jr.
*Assistant Examiner*—Carol A. Salata
*Attorney, Agent, or Firm*—Cushman, Darby & Cushman

[57] ABSTRACT

A polypeptide comprising repeated amino acid sequences of a cell-adhesive protein represented by the formula:

(Arg-Gly-Asp)n or (Tyr-Ile-Gly-Ser-Arg)n wherein n is a number ranging from 2 to 20; or a pharmaceutical acceptable salt thereof, which is valuable as an antimetastatic agent for cancer.

4 Claims, 1 Drawing Sheet

POLYPEPTIDE COMPRISING REPEATED CELL-ADHESIVE CORE SEQUENCES

This is a division of U.S. application Ser. No. 07/370,182, filed Jun. 23, 1992, now U.S. Pat. No. 5,183,804.

FIELD OF THE INVENTION

This invention relates to a polypeptide comprising repetition of a certain amino acid sequence which consists of the adhesive core of cell-adhesive proteins, as well as to the use of said polypeptide in various drugs including an antimetastatic agent for cancer.

PRIOR ART

Some proteins such as fibronectin, laminin and vitronectin relate to the adhesion between cells and interstitial connective tissues and exert various physiological activities relating to the cellular functions of animal cells. These proteins are generally called cell-adhesive proteins. For example, fibronectin is a glycoprotein which is synthesized in liver and occurs at a concentration of approximately 0.3 mg/ml in human plasma.

Fibronectin comprises a dimer of polypeptide chain A having a molecular weight of approximately 250K and chain B having a molecular weight of approximately 240K which are connected in the vicinity of each of the carboxyl-ends through disulfide bonds. Kornblihtt, A. R. et al. determined the primary structure of fibronectin by molecular cloning techniques [EMBO Journal, 4, 1755 (1985)]. On the other hand, the primary structure of laminin was determined by Sasaki, M. et al. [Proc. Natl. Acad. Sci. U.S.A., 84, 935 (1987); and J. Biol. Chem., 262, 17111 (1987)], and the primary structure of vitronectin was determined by Suzuki, S. et al. [EMBO Journal, 4, 2519 (1985)].

Further studies were made on the binding sites relating to cell-adhesion activity. The binding sites of both of the chains A and B were determined by partially digesting fibronectin with proteases and then examining the binding of the fragments thus obtained to heparin, collagen, cells and bacteria [Yamada, K. M., Ann. Rev. Biochem., 52, 761 (1983)]. Furthermore, it was clarified in 1984 that the core sequence of the cell-binding site of these chains was Arg-Gly-Asp (RGD) [Pierschbacher, M. D. et al., Nature, 309, 30 (1984)]. It has been known that this RGD sequence also occurs in other adhesive proteins such as vitronectin. It has been also clarified that the core sequence of the cell-binding site of laminin is Tyr-Ile-Gly-Ser-Arg [Graf, J. et al., Cell, 48, 989 (1987)].

Thus fibronectin and laminin adhere to receptors of cells via the above-mentioned core sequence and transmit some information to the cells to which they adhere. In addition, it is believed that these substances are capable of binding to biopolymers such as heparin, collagen and fibrin, and thus relate to the adhesion between cells and interstitial connective tissues and to the differentiation and growth of cells [Yamada, K. M., Ann. Rev. Biochem., 52, 761 (1983)].

Attempts have been made to apply these cell-adhesive proteins having the various biological activities described above to many purposes including medical ones. For example, a decrease in plasma fibronectin level would lower the reticuloendothelial function. This phenomenon is observed in, for example, septicemia induced by surgical operation or trauma, intravascular coagulation disseminate, burns, serious infectious diseases and surgical shock. It seems, therefore, that the administration of fibronectin is an effective way of ameliorating these conditions. Further fibronectin is expected to be applicable to the treatment of wounds and to immunomodulation, since it activates the migration of fibroblasts and macrophages. An attempt to apply fibronectin, which would promote the healing of wounds, to topical treatment of corneal disorders has already been made [Fujikawa, L. S. et al., Lab. Invest., 45, 120 (1981)].

On the other hand, laminin is capable of binding to collagen IV, heparin sulfate, proteoglycans and cells. Additionally, laminin exerts an effect of promoting the elongation of axons of neurons. Thus its effects in vivo are extremely interesting.

Furthermore, cell-adhesive proteins have attracted attention since they relate to the metastasis of cancer. During the metastasis stage of cancer, cancer cells come in contact with various cells or biopolymers. When cell-adhesive proteins such as fibronectin or laminin are present at this stage, the cancer cells would form a multicellular mass, which allows growth or survival of the cancer cells. In fact, it has been observed that the administration of laminin mixed with cancer cells to an animal accelerated the metastasis of cancer.

In contrast to these phenomena, however, it has been reported that a fragment obtained by digesting laminin with proteases acts to inhibit the metastasis of cancer [Barsky, S. H. et al., J. Clin, Invest., 74, 843 (1984)]. It has likewise been confirmed that a tripeptide Arg-Gly-Asp corresponding to the adhesive core sequence of fibronectin [(Humphries, M. J. et al., Science, 233, 467 (1986)] and a pentapeptide Tyr-Ile-Gly-Ser-Arg corresponding to that of laminin [Iwamoto, Y. et al., Science, 238, 1132 (1987)] act to inhibit the metastasis of cancer.

As described above, cell-adhesive proteins such as fibronectin and laminin have various biological activities. Thus it is required to develop techniques for the application of substances related to them as drugs. It is believed that the antimetastatic effects of the adhesive core sequences of fibronectin and laminin are highly useful as drugs. However, the cell-adhesive activities of said core sequences are still unsatisfactory in practical applications from the medical viewpoint. Accordingly, it has been required to develop a substance exhibiting improved activity. However, these cell-adhesive proteins are natural substances and thus the supply thereof is restricted. In addition, it is considerably difficult to efficiently produce these glycoproteins through chemical synthesis or genetic engineering techniques.

SUMMARY OF THE INVENTION

The present invention provides a novel compound which sustains at an adequate level various biological activities observed in cell-adhesive proteins, which can be easily synthesized, and which causes no serious side effects on living organisms. The compound of the present invention is a polypeptide compound having high antimetastatic activity as compared with the above-mentioned core sequences. In addition to its antimetastatic activity, the compound of the present invention is also effective in immunomodulation, healing of wounds, inhibition of platelet agglutination and neuriatria.

Accordingly, the present invention provides a novel polypeptide compound having a relatively low molecular weight which can be easily produced and has various activities similar to those of cell-adhesive proteins.

Further, the present invention provides a novel polypeptide compound having a high antimetastatic activity.

Furthermore, the present invention provides a pharmaceutical composition comprising said novel polypeptide compound.

DETAILED DESCRIPTION OF THE INVENTION

Figure 1:
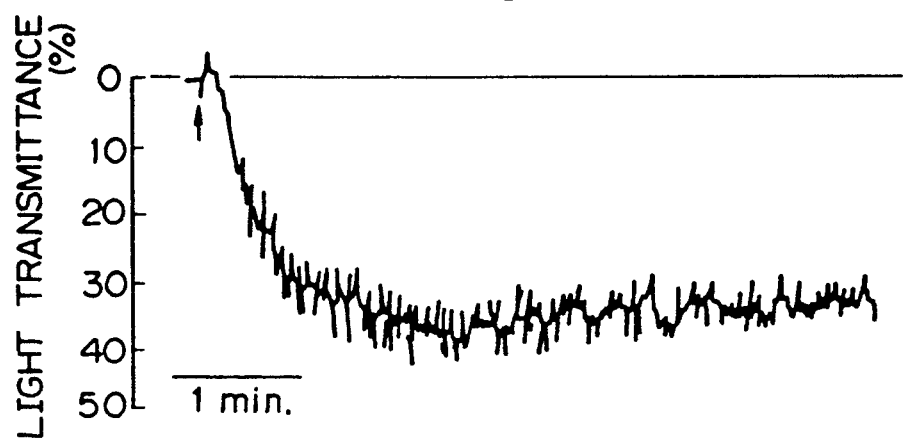
FIG. 1 is a graph which shows the effect of PBS (a control) on cancer-induced platelet aggregation.

The polypeptide of the present invention is characterized by comprising repeated adhesive core amino acid sequences of cell-adhesive proteins. In one embodiment, a preferable polypeptide compound of the present invention is represented by the following formula:

(Arg-Gly-Asp)n wherein n represents a number ranging from 2 to 20. Among the compounds of the above formula, those having a molecular weight of approximately 1,000 to 10,000, in particular, approximately 1,500 to 5,000, are preferable, since they have sufficiently high biological activities and are highly soluble in aqueous solvents.

In another embodiment, the compound of the present invention is represented by the following formula:

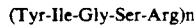

(Tyr-Ile-Gly-Ser-Arg)n wherein n represents a number ranging from 2 to 20. Among the compounds of the above formula, those having a molecular weight of approximately 5,000 to 15,000, in particular, approximately 10,000, are preferable for the same reasons as those described above.

Preparation

The compound of the present invention may be prepared by polymerizing a corresponding short-chain peptide obtained in a conventional manner, for example, Arg-Gly-Asp or Tyr-Ile-Gly-Ser-Arg by a continuous polymerization method utilizing diphenylphosphoryl azide (DPPA) [Nishi, N. et al., Int. J. Biol. Macromol., 2, 53 (1980); and Nishi N. et al., Int. J. Peptide Protein Res., 30, 275 (1987)].

Alternatively, the compound of the present invention may be obtained through genetic engineering techniques.

The polypeptide compound of the present invention may consists of either L- or D-amino acids. Since the compound of the present invention is to be used as a drug, it may be converted into pharmaceutically acceptable salts, e.g., inorganic acid salts such as hydrochloride or sulfates or organic acid salts such as acetate, trifluoroacetate, lactate or tartrate. The conversion of the compounds into these salts may be conducted by utilizing conventional methods.

Action

The polypeptide compound of the present invention having the repeated cell-adhesive protein core sequences adheres to cells via said core sequences through the same mechanism as the one observed in the case of cell-adhesive proteins. Thus the compound of the present invention shows various biological activities as an agonist or an antagonist of said cell-adhesive proteins. It should be noted here that the compound of the present invention has an anti-metastatic effect 6 to 10 times as high as that of the cell-adhesive protein core sequences. Furthermore, the pelypeptide compound of the present invention has a wide range of biological activities. Namely, it is effective in immunomodulation, healing of wounds, inhibition of intravascular platelet aggregation caused by cancer cells and alleviation of neuro-disorders. It showed no toxicity when examined in experiments with mice.

Accordingly, at least one of the polypeptide compounds of the present invention, optionally together with suitable conventional carriers or pharmaceutical adjuvants, can be administered to a patient as an antimetastatic agent for cancer, a remedy for wounds, an immunomodulator, a platelet aggregation inhibitor or an alleviator for neuro-disorders. The dose may be determined depending on the condition, age, body weight etc. of the patient within the range of 0.2 $\mu$g/kg to 400 mg/kg.

The method of administering the polypeptide of the present invention may preferably be selected from those commonly used for peptide drugs, for example, parenteral administration methods such as intravenous, intramuscular or subcutaneous administration. The polypeptide compound of the present invention may be formulated into an injection suitable for the above-mentioned administration methods by, for example, the following method. It is dissolved in PBS or physiological saline solution, as will be shown hereafter, to thereby give an injection. Alternatively, it may be dissolved in, for example, a 0.1N aqueous solution of acetic acid and then lyophilized. These preparations may further contain conventional stabilizers such as glycine or albumin. Furthermore, collagen or a liposome may be used as a carrier in order to prolong the half-life of the compound of the present invention in blood.

Alternatively, the polypeptide of the present invention may be formulated into microcapsules for oral administration by, for example, encapsulation in a liposome. Furthermore, it may be absorbed through mucosa other than the digestive tract by formulating into, for example, suppositories, sublingual tablets or nasal sprays.

Evaluation of Biological Activity

Now the biological activities of the compound of the present invention will be described based on the results of pharmacological tests.

(1) Adhesiveness to Target Cells

The adhesiveness to target cells of the compound of the present invention was examined in accordance with a method reported by Saiki et al. [Cancer Immunol., Immunother., 22, 125 (1986)]. Namely, a polypeptide of the present invention having a structure of (Arg-Gly-Asp)n and a molecular weight of approximately 5,000 prepared in the following Synthetic Example 1 and a comparative polypeptide, (Arg, Gly, Asp)n, carrying a random sequence of the corresponding amino acids Arg, Gly and Asp and having a molecular weight of approximately 5,000 prepared in the following Synthetic Example 3 were employed. The adhesiveness of each compound was examined by using mouse B16-Bl6 melanoma cells as the target.

First, microculture wells were preliminarily coated with 20 μg/ml of the polypeptide to be examined or 5 μg/ml of mouse fibronectin (obtained from Seikagaku Kogyo, Japan) which was used as a positive control. Next 0.05 ml/well of B16-BL6 melamona cells ($2 \times 10^4$) labeled with a radioactive iodide [$^{125}$I]IUdR was added thereto and the cells were cultured at 37° C. for 20 minutes. The number of cells thus adsorbed by the culture wells was determined by measuring the radioactivity. 1% bovine serum albumin (BSA) was employed as a negative control. The B16-BL6 melanoma cells were labeled by culturing the cells to be labeled at the logarithmic growth phase for 24 hours in an MEM medium containing 5% of FBS and 0.3 μCi/ml of [$^{125}$I]IUdR (200 mCi/mmol; obtained from New England Nuclear, Boston, Mass., USA).

The labeled cells were washed with physiological saline solution twice and suspended in 0.02% EDTA for 1 minute. Subsequently the cells were collected and suspended in a serum-free MEM medium. The cell suspension thus obtained was used in the above examination. The unadsorbed cells in the well were washed away with PBS 4 times. Then the cells adsorbed by the well were dissolved in 0.1 ml of 0.1N NaOH. The number of adsorbed cells was determined by measuring the radioactivity of the dissolved cells.

Table 1 shows the results. As Table 1 indicates, the Poly(Arg-Gly-Asp) of the present invention and fibronectin accelerated the adsorption of the B16-BL6 melanoma cells, while the treatment with the Poly(Arg, Gly, Asp) having the random sequence and BSA caused scarcely any adsorption of the cells. These results indicate that the cell-adhesion activity of the polypeptide of the present invention is comparable to that of fibronectin.

TABLE 1

Adhesion of B16-BL6 melanoma cells to substrate coated with polypeptide or fibronectin

| Coating | Incubated with | Adhesiveness adhered cell No./ substrate (SD) |
|---|---|---|
| Fibronectin | | 5849 ± 513 |
| Poly(Arg—Gly—Asp) | | 7967 ± 910 |
| Poly(Arg, Gly, Asp) | | 1750 ± 395 |
| BSA | | 1239 ± 347 |
| Fibronectin | | |
| + Arg—Gly—Asp | 500 μg/ml | 3708 ± 265 (37%) |
| | 100 | 5320 ± 52 |
| + His—Gly—Gly | 500 | 6133 ± 787 |
| + Poly(Arg—Gly—Asp) | 500 | 3715 ± 231 (36%) |
| | 100 | 3687 ± 229 (37%) |

Table 1 also shows the results of examination of the cell adhesion specificities of the Poly(Arg-Gly-Asp) and fibronectin. Namely, $2 \times 10^4$ B16-BL6 cells were added to culture cells which had been treated in the same manner as the one described above. These cells were then cultured therein at 37° C. for 20 minutes in the presence of 100 or 500 μg/ml of a synthetic peptide Arg-Gly-Asp, 100 or 500 μg/ml of the Poly(Arg-Gly-Asp) or 500 μg/ml of His-Gly-Gly. It was thus found that the adhesion of the fibronectin to the cells was inhibited when they were cultured in the presence of the Arg-Gly-Asp or Poly(Arg-Gly-Asp) whereas no inhibition was observed in the presence of the His-Gly-Gly (refer to Table 1).

The cell-adhesiveness of fibronectin was dose-dependently inhibited by using the synthetic tripeptide Arg-Gly-Asp. Furthermore, it was also inhibited by 5 mM EDTA. These results indicate that the cell adhesion mechanism of the Poly(Arg-Gly-Asp) would be specifically dependent on divalent metal ions such as calcium and magnesium ions and Arg-Gly-Asp sequence. Namely, it was suggested that the Poly(Arg-Gly-Asp) adheres to cells via the same receptor as the one which takes part in the adhesion of fibronectin to cells.

Thus the results of the above examination suggested that the polypeptide compound of the present invention may be applicable to drugs as an agonist or an antagonist of fibronectin.

(2) Antimetastatic Effect (a) Next, the antimetastatic effect on cancer of the compound of the present invention having repeated core sequences Arg-Gly-Asp was examined. A 500 μg portion each of a synthetic polypeptide Poly(Arg-Gly-Asp) having a molecular weight of approximately 5,000, a tripeptide Arg-Gly-Asp and a polypeptide Poly(Arg, Gly, Asp) having a molecular weight of approximately 5,000 was mixed with $5 \times 10^4$ B16-BL6 melanoma cells which were in the above-mentioned logarithmic growth phase and showed extremely strong metastasis, in PBS. 0.2 ml of each mixture thus obtained was intravenously injected into a group of male C57BL/6 mice. Each group consisted of five animals. Fourteen days after the administration, the cancer colonies in the lungs of the animals were counted and the obtained data were compared with those of a control group which received PBS alone. The results are given in Table 2-1 (Test 1). As the results indicate, the metastasis of cancer to lungs was remarkably inhibited by the administration of the Poly(Arg-Gly-Asp). In contrast thereto, the administration of either Arg-Gly-Asp or Poly(Arg, Gly, Asp) showed no such antimetastatic effect. Table 2-1 further indicates that the amount of Arg-Gly-Asp needed to achieve an antimetastatic effect comparable to that of the Poly(Arg-Gly-Asp) is 3,000 μg, i.e., approximately 6 times as much as that of the polypeptide compound of the present invention.

(b) Next, the antimetastatic activities of two polypeptides each having repeated Arg-Gly-Asp sequences, namely, Poly(Arg-Gly-Asp)-1500 (approximate molecular weight: 1,500) and Poly(Arg-Gly-Asp)-5000 (approximate molecular weight: 5,000) were examined. 1,000 μg of each compound was administered to mice in the same manner as described in the above Test 1 and the effects were observed. As Table 2-1 (Test 2) indicates, both of the compounds used in Test 2 showed a remarkable antimetastatic effect compared with the control group.

Furthermore, Poly(Arg-Gly-Asp)-5000 was not mixed with B16-BL6 cells but intravenously administered to mice to which B16-BL6 cells had been administered 5 minutes before. In this case also, a high antimetastatic effect was observed. This fact indicates that the administration of the compound of the present invention in appropriate manner, such as intravenous injection, would give an antimetastatic effect.

TABLE 2-1

Effect of polypeptides on experimental metastasis of cancer induced by injecting B16–BL6 melanoma cells

| Compound | Administration | Dose (μg) | Metastasis to lung mean ± SD (range) |
|---|---|---|---|
| Test 1 | | | |
| PBS (untreated) | — | — | 91 ± 19 (64–112) |
| Poly(Arg—Gly—Asp) | simultaneous | 500 | 23 ± 3 (20–28)* |
| Arg—Gly—Asp | simultaneous | 3000 | 18 ± 24 (1–52)* |
|  |  | 500 | 46 ± 14 (33–68) |
| Poly(Arg, Gly, Asp) | simultaneous | 500 | 65 ± 4 (64–68) |
| Test 2 | | | |
| PBS (untreated) | — | — | 52 ± 8 (40–60) |
| Poly(Arg—Gly—Asp) (m.w.: 5,000) | simultaneous | 1000 | 6 ± 4 (2–14)* |
|  | separate | 1000 | 16 ± 4 (10–20)* |
| Poly(Arg—Gly—Asp) (m.w.: 1,500) | simultaneous | 1000 | 14 ± 4 (10–18)* |

*p < 0.001 when compared with untreated control in Student's t-calibration.

(c) Next, the antimetastatic effect of a polypeptide compound Poly(Tyr-Ile-Gly-Ser-Arg) obtained in Synthetic Example 4 described hereafter, which had a molecular weight of approximately 10,000 and a cell-adhesive core sequence of laminin (Tyr-Ile-Gly-Ser-Arg), was also examined. Namely, portions of 2, 20 and 100 μg of the above compound were each mixed with $3 \times 10^4$ Lewis lung cancer cells (3 LL) and administered to a group of C57BL/6 mice in the same manner as the one described in the above (b). Thus the antimetastatic effect of this compound was examined. Table 2—2 shows the results. As Table 2—2 indicates, the metastasis of cancer to the lungs was remarkably inhibited by the administration of the Poly(Tyr-Ile-Gly-Ser-Arg). In contrast thereto, the administration of 100 μg of a pentapeptide Tyr-Ile-Gly-Ser-Arg showed scarcely any antimetastatic effect. Though this result is not shown in the above Table, it was required to administer at least 200 μg of this compound in order to achieve a significant effect. These results indicate that the polypeptide of the present invention having the repeated pentapeptide sequences has an antimetastatic activity almost 10 times as high as that of the original pentapeptide.

TABLE 2-2

Effect of polypeptides on experimental metastasis induced by injecting metastatic cancer cells

| Cancer | Administered compound | Dose (μg/animal) | No. of instances of metastasis to lung mean ± SD (range) |
|---|---|---|---|
| B16–BL6 | Untreated (PBS) | — | 115 ± 24 (86–149) |
|  | Poly(Tyr—Ile—Gly—Ser—Arg) | 100 | 19 ± 9 (10–32)* |
|  |  | 20 | 43 ± 13 (24–56)* |
|  |  | 5 | 81 ± 9 (67–89)** |
|  | Tyr—Ile—Gly—Ser—Arg | 100 | 101 ± 17 (77–122) |
|  |  | 20 | 109 ± 39 (61–164) |
|  |  | 5 | 128 ± 31 (104–180) |
| 3LL | Untreated (PBS) | — | 139 ± 19 (113–158) |
|  | Poly(Arg—Gly—Asp) | 500 | 34 ± 7 (26–41)* |
|  | Poly(Tyr—Ile—Gly—Ser—Arg) | 100 | 14 ± 11 (2–28)* |
|  | Tyr—Ile—Gly—Ser—Arg | 100 | 123 ± 45 (74–187) |

*p < 0.001 when compared with untreated control in Student's t-calibration.
**p < 0.02 when compared with untreated control in Student's t-calibration.

(3) Inhibitory Effect on Cancer Cell Retention in Lungs

An examination similar to the one described above proved that the compound of the present invention has an inhibitory effect on the retention of cancer cells in lungs. B16–BL6 cells at the logarithmic growth phase were labeled with [$^{125}$I]IUdR. 0.2 ml portions of a solution containing $2 \times 10^4$/mouse of these labeled cells and 500 μg/mouse of Poly(Arg-Gly-Asp) having a molecular weight of 5,000 were intravenously injected in the tails of C57BL/6 mice. The liver, kidneys, spleen and lungs of each animal were removed 30 minutes or 24 hours after the administration and the radioactivity in these organs was determined. Mice which received PBS were used as control animals. Table 3 shows the results. The radioactivity of the lungs of the Poly(Arg-Gly-Asp) administration group was markedly lower than that of the control group, though no significant difference was observed in other organs including blood. This fact indicated that the retention of the cancer cells in the lungs was significantly inhibited in the test group.

TABLE 3

Distribution and retention of [$^{125}$I]IUdR-labeled B16-BL6 melanoma cells administered together with Poly(Arg—Gly—Asp) to C57BL/6 mice

| Organ | Radioactivity (cpm ± SD)* | |
|---|---|---|
|  | Untreated (PBS) | Poly(Arg—Gly—Asp) |
| Lung | 2034 ± 284 (13.2%)** | 1121 ± 281 (7.3%)*** |
| Liver | 260 ± 30 (1.7%) | 195 ± 42 (1.3%) |
| Spleen | 38 ± 12 (0.2%) | 59 ± 7 (0.4%) |
| Kidney | 78 ± 2 (0.5%) | 73 ± 19 (0.5%) |
| Blood (1 ml) | 560 ± 260 (3.7%) | 304 ± 94 (2.0%) |

*Average of 3 animals.
**Percentage relative to the administered radioactivity (15308 ± 1605 cpm/2 × $10^4$ cells) is given in parenthesis.
***p < 0.02 in Student's t-calibration when compared with the untreated (PBS) group.

(4) Antimetastatic Effect on Spontaneous Metastasis Model

Furthermore, the antimetastatic effect of the compound of the present invention on a spontaneous metastasis model was examined. Namely, B16–BL6 cells were transplanted into the foot pads of C57BL/mice (each group having five animals). Then 100 μg or 50 μg of Poly(Arg-Gly-Asp) having a molecular weight of approximately 5,000 was topically administered directly to the site of the transplanted cancer in each animal in a single or divided dose within a determined period. The transplanted cancer was removed on the 21st day and the mouse was anatomized 2 weeks later to examine the metastasis of the cancer into the lungs. Table 4 shows the results. It was found that the metastasis of the cancer to the lungs was remarkably reduced, though the growth of the transplanted cancer per se could not be suppressed, by administering 100 μg of the compound on the 1st or 7th day in a single dose or by administering 50 μg portions of the same of the 7th, 10th, 13th and 16th days.

In contrast, the administration of 100 μg of Poly(Arg, Gly, Asp) having a random amino acid sequence on the 7th day did not suppress the metastasis of cancer into the lungs at all.

TABLE 4

Inhibitory effect of polypeptides on spontaneous metastasis of B16-BL6 melanoma cells administered to foot pad

| Compound | Dose (μg/ animal) | Administration date | Observation on 21st day | |
|---|---|---|---|---|
| | | | Size of transplanted cancer (mm ± SD) | Number of metastatic cancer to lung (mm ± SD) |
| Untreated (PBS) | | | 10 ± 4 | 129 ± 38 (78–180) |
| Poly(Arg—Gly—Asp) | 100 | 1 | 8 ± 4 | 24 ± 17 (4–49)* |
| | | 7 | 9 ± 3 | 29 ± 22 (0–50)* |
| | | 14 | 10 ± 4 | 120 ± 29 (70–155) |
| | | 20 | 8 ± 3 | 131 ± 79 (75–247) |
| | 50 × 4 | 7, 10, 13, 16 | 8 ± 3 | 26 ± 29 (0–68)* |
| Poly(Arg, Gly, Asp) | 100 | 7 | 11 ± 3 | 158 ± 62 (117–230) |

*p < 0.001 in Student's t-calibration when compared with untreated control.

(5) Suppressive Effect on Platelet Aggregation Indicated by Cancer Cells

Figure 2:
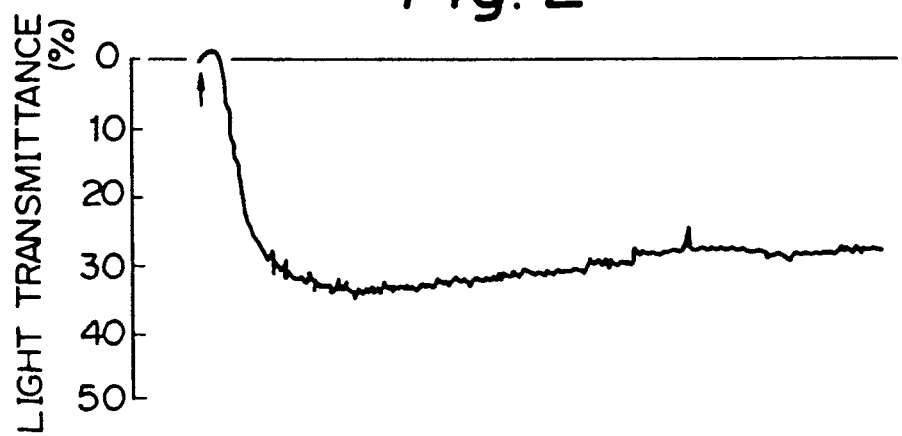
FIG. 2 is a graph which shows the effect of Poly-(Arg, Gly, Asp) (a comparative compound) on cancer-induced platelet aggregation.
Figure 3:
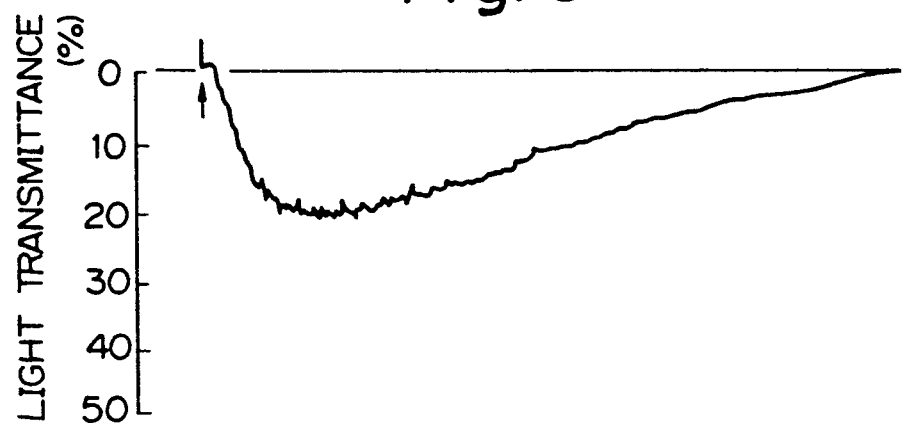
FIG. 3 is a graph which shows the effect of Poly-(Arg-Gly-Asp) (the compound of the present invention) on cancer-induced platelet aggregation.

The effect of Poly(Arg-Gly-Asp) on the platelet aggregation induced by cancer cells was examined. The blood of a C57BL/6 mouse was centrifuged at 160×g for 15 minutes to give platelet rich plasma (PRP). As a control, platelet poor plasma (PPP) obtained by centrifuging the blood at 1,000×g for 10 minutes was employed. Poly(Arg-Gly-Asp) having a molecular weight of 5,000 was added to 250 μl of the above PRP or PPP plasma ($5 \times 10^5/\mu l$). After preincubation for 5 to 7 minutes, the mixture was added to a suspension of B16-BL6 cells in physiological saline (approximately $10^6$/ml) and stirred at 37° C. at 1,000 rpm. During this period, the aggregation of the platelets was monitored with a dual aggregometer (Model 440; Chrono-Log, USA). For comparison, the above procedure was repeated replacing the Poly(Arg-Gly-Asp) with Poly(Arg, Gly, Asp). FIGS. 1 to 3 together show the results. FIGS. 1, 2 and 3 respectively show the platelet aggregation observed when the heparinized PRP was treated with PBS; with 100 μg/ml of Poly(Arg, Gly, Asp); and with 100 μg/ml of Poly(Arg-Gly-Asp); 7 minutes prior to the addition of the B16-BL6 melanoma cells (shown by an arrow) in each case. As these figures indicate, the compound of the present invention Poly(Arg-Gly-Asp) completely suppressed the platelet aggregation (FIG. 3), while the comparative one Poly(Arg, Gly, Asp) showed scarcely any suppression capability (FIG. 2).

(6) Toxicity

The above tests (1) to (5) proved that the Poly(Arg-Gly-Asp) having a molecular weight of 5,000 or 1,500 and the Poly(Tyr-Ile-Gly-Ser-Arg) having a molecular weight of 10,000 showed neither any cytotoxicity on erythrocytes, spleen and thymus cells nor any undesirable aggregation effect on serum proteins.

Formulation

As stated above, the polypeptide of the present invention is, like other pharmaceutical peptides, preferably administered parenterally in the form of an injection for intravenous, intramascular or subcutaneous administration. Alternatively, the peptide can be administered orally in the form of a microcapsule containing the peptide in liposome or can be administered by absorption through mucous membranes other than digestive tracts in the form of a suppository, sublingual agent or nasal spray.

Following formulations are given as non-limiting examples of the invention.

| A) Injectable solution Composition | |
|---|---|
| Peptide of the invention | 2 g |
| Sodium chloride | 8 g |
| Ascorbic acid | 2 g |
| Sterile water | 1 l |

The peptide, ascorbic acid and sodium chloride were dissolved in sterile water, an ampule was filled with 5 ml of the solution and then sealed to afford an injectable solution.

| B) Lyophilizate Composition | |
|---|---|
| Peptide of the invention | 2 g |
| Sorbitol | 20 g |

The peptide and sorbitol were dissolved in 200 ml of sterile water, a vial was filled with 1 ml of the solution and lyophilized, and the vial was then sealed. This composition can be dissolved in 5 ml of sterile water before parenteral administration.

SYNTHETIC EXAMPLE

Now examples of the process of preparing the compound of the present invention will be described. Amino acid derivatives were purchased from Peptide Institute, Inc. (Hinoh-shi, Osaka, 562 Japan), while peptides were synthesized by the liquid phase method. The evaluation of the purity of polypeptides and the identification of each compound were conducted by thin layer chromatography [developing solvent: (A) the upper layer of a mixture of n-butanol:acetic acid:water=4:1:5; (B) n-butanol: pyridine:acetic acid:water=15:10:3:12; (C) aqueous ammonium-saturated n-butanol etc.], elementary analysis and infrared spectrometry. Polypeptides having regular sequences or random sequences were synthesized by the method based on use of dipheylphosphoryl azide (DPPA). The protecting groups (Mts and Bzl groups) of the side-chain functional groups were removed by utilizing methanesulfonic acid/anisole or trifluoromethanesulfonic acid/thioanisole. Finally, the guanide group in the arginine side chain was converted into hydrochloride with an ion exchange resin (Amberlite IRA-400). The removal of the protecting groups was confirmed by infrared spectrometry. The molecular weight was roughly estimated by polyacrylamide gel electrophoresis (gel concentration: 15% or 20%) in the presence of 1% of sodium dodecyl sulfate.

SYNTHETIC EXAMPLE 1

Polypeptide (m.w.: ca. 5,000)

(1) t-Butoxycarbonylglycyl-β-benzyl-L-aspartic acid
[Boc-Gly-Asp(OBzl)-OH] (I)

5.3 g (30 mmol) of t-butoxycarbonyl glycine was dissolved in 100 ml of purified THF and 4.6 ml (33 mmol) of triethylamine and 4.33 ml (33 mmol) of isobutyl chloroformate) were added thereto at −15° C. The mixture was stirred at this temperature for 10 minutes. To the resultant solution of a mixed acid anhydride was added a solution which had been prepared by dissolving 8.0 g (36 mmol) of β-benzyl-L-aspartic acid and 5.02 ml (36 mmol) of triethylamine in water and cooling to 0° C. The mixture was then stirred at 0° C. for 1 hour and further at room temperature for 15 hours. After removing the THF by concentration under reduced pressure, cold 10% citric acid was added thereto. The precipitate thus formed was extracted with ethyl acetate twice. The extracts were combined and washed 5 times with one fifth the volume of 5% citric acid and then 10 times with water (one tenth the volume thereof). The solution was dehydrated over anhydrous sodium sulfate and concentrated to dryness. Then the residue was dissolved in ether and precipitated with n-hexane. After repeating this precipitation procedure 3 times, the obtained product was dried, whereby 6.9 g of the titled compound was obtained.

(2) Glycyl-β-benzyl-L-aspartate hydrochloride
[HCl.H-Gly-Asp(OBzl)-OH] (II)

3.2 g of compound (I) as obtained in the above step (1) was dissolved in 80 ml of purified dioxane. After adding 80 ml of 4N HCl/dioxane, the mixture was stirred at room temperature for 1 hour. After concentrating to dryness, dry ether was added thereto whereby the product was crystallized, which was then collected by centrifugation and washed with dry ether several times. Thus 2.4 g of the titled compound was obtained.

(3) $N^{\alpha}$-t-butoxycarbonyl-$N^{107}$-mesitylenesulfonyl-L-arginylglycyl-β-benzyl-L-aspartate [Boc-Arg(Mts)-Gly-Asp(OBzl)-OH] (III)

3.4 g (7.4 mmol) of $N^{\alpha}$-t-butoxycarbonyl-$N^{\omega}$-mesitylenesulfonyl-L-arginine was dissolved in 70 ml of purified THF and 1.13 ml (8.1 mmol) of triethylamine and 1.07 ml (8.1 mmol) of isobutyl chloroformate were added thereto at −15° C. The resultant mixture was stirred at this temperature for 10 minutes to allow a mixed acid anhydride to be formed. 2.4 g (approximately 8.0 mmol) of compound (II) as described in the above step (2) and 2.68 ml (19.2 mmol) of triethylamine were dissolved in a solvent mixture comprising 70 ml of THF, 50 ml of DMF and 10 ml of water and cooled to 5° C. This solution was added to the above-mentioned mixed acid anhydride solution and the mixture was stirred at 5° C. for 1 hour followed by stirring at room temperature for 15 hours. After removing the THF and water by concentration under reduced pressure, 5% citric acid was added to the residual DMF solution. The precipitate thus formed was separated by decantation, thoroughly washed with 5% citric acid and water and dried. After washing with ether twice, the residue was reprecipitated from methanol/ether and separated by decantation. The precipitate was converted into a powder by treating with ether. This powder was then centrifuged, washed with ether and dried. Thus 3.9 g of the titled compound was obtained.

(4) $N^{\omega}$-mesitylenesulfonyl-L-arginylglycyl-β-benzyl-L-aspartate hydrochloride
[HCl.H-Arg(Mts)-Gly-Asp(OBzl)-OH] (IV)

1.5 g (2.1 mmol) of compound (III) was dissolved in 30 ml of purified dioxane and 30 ml of 4N HCl/dioxane was added thereto. The mixture was stirred for 1 hour. After concentrating to dryness, the product was crystallized by adding dry ether. The crystals were centrifuged, washed with dry ether several times and dried. Thus 1.3 g of the titled compound was obtained.

(5) L-arginylglycylaspartate hydrochloride
(2HCl.H-Arg-Gly-Asp-OH) (V)

300 mg of compound (III) was dissolved in a mixture of 4 ml of methanesulfonic acid and 1 ml of anisole and the resultant solution was stirred at room temperature for 1.5 hours. After adding dry ether, the precipitate thus formed was separated by decantation, thoroughly washed with dry ether and dried. The product was dissolved in a small amount of water and passed through a column packed with Amberlite IRA-400 (Cl form). Then a fraction containing the target compound was concentrated to dryness and the residue was crystallized by treating with methanol/ether. After centrifuging, washing with ether and drying, 117 mg of the titled compound was obtained.

(6) Poly($N^{\omega}$-mesitylenesulfonyl-L-asparginylglycyl-β-benzyl-L-aspartate) [Poly(Arg(Mts)-Gly-Asp(OBzl)] (VI)

400 mg (0.58 mmol) of the compound (IV) was dissolved in 1.2 ml of purified DMSO and 0.19 ml (0.87 mmol) of DPPA and 0.285 ml (2.03 mmol) of triethylamine were added thereto. The obtained mixture was stirred at 5° C. to 8° C. for 1 hour followed by stirring at room temperature for 2 days. Next, DPPA and triethylamine were again added thereto each in the same amount. The polymerization was continued for a further 2 days. The polymer thus formed was precipitated with water, centrifuged, thoroughly washed with water and methanol, and dried. Thus 295 mg of the titled compound was obtained.

(7) Poly(L-arginylglycyl-L-aspartate hydrochloride)
[Poly(Arg-Gly-Asp)HCl] (VII)

100 mg of compound (VI) was treated with a mixture of 2 ml of methanesulfonic acid and 0.4 ml of anisole in order to remove the protecting group in the side chain. Then the position was converted into the hydrochloride by treating with an anion exchange resin. The process used for the synthesis of compound (V) was repeated. Thus 60 mg of the titled compound having a molecular weight of approximately 5,000 was obtained.

SYNTHETIC EXAMPLE 2

Comparative Compound with Random Sequence (1) Copoly($N^{\omega}$-mesitylenesulfonyl-L-arginine, glycine, β-benzyl-L-aspartate) [Copoly(Arg(Mts), Gly, Asp(OBzl)] (VIII)

A mixture comprising 356 mg (1.0 mmol) of $N^{\omega}$-mesitylenesulfonyl-L-arginine, 75 mg (1.0 mmol) of glycine and 223 mg (1.0 mmol) of β-benzyl-L-aspartate was polymerized with 0.97 ml (4.5 mmol) of DPPA and 1.05 ml (7.5 mmol) of triethylamine in 2.0 ml of purified DMSO. The process employed for the synthesis of compound (VI) was repeated.

(2) Copoly(L-arginine hydrochloride, glycine, L-aspartic acid) [Copoly(Arg, Gly, Asp)HCl] (IX)

100 mg of compound (VIII) was treated with a mixture of 2 ml of methanesulfonic acid and 0.4 ml of anisole to remove the protecting groups in the side chain. Then the positions were converted into the hydrochlorides by treating with an ion exchange resin. The process employed for the synthesis of compound (V) was repeated. Thus 50 mg of the titled compound having a molecular weight of approximately 5,000 was obtained.

SYNTHETIC EXAMPLE 3

Polypeptide (m.w.: ca. 1,500)
Poly(L-arginyl-glycyl-L-aspartic acid)hydrochloride [Oligo(Arg-Gly-Asp).HCl] (X)

The polymerization of compound (VI) was ceased 90 minutes after initiation. The oligopeptide having a protected side chain thus obtained was treated in the same manner as the one described in the synthesis of compound (VII). Thus the titled compound having an average molecular weight of approximately 1,500 was obtained.

SYNTHETIC EXAMPLE 4

Polypeptide (m.w.: ca. 10,000)

(1) $N^\omega$-mesitylenesulfonyl-L-arginine-O-methylester hydrochloride [HCl-Arg(Mts)-OMe] (XI)

2.10 g of $N^\alpha$-t-butoxycarbonyl-$N^\omega$-mesitylenesulfonyl-L-arginine [Boc-Arg(Mts)-OH] was dissolved in 31 ml of dry dioxane and 31 ml of 4N HCl-dioxane was added thereto. The obtained mixture was stirred at room temperature for 1 hour. The resulting solution was concentrated under reduced pressure to dryness and then crystallized by adding dry ether. The target product was collected by centrifugation, washed with dry ether several times and dried in a desiccator. Thus 1.1 g of HCl.H-Arg(Mts)-OH from which Boc groups had been removed was obtained. This product was next added to a solution, which had been prepared by slowly adding 2.9 ml of $SOCl_2$ to 10.6 ml of methanol and stirring at $-10°$ C. for 10 minutes, and the obtained mixture was stirred for 15 hours, concentrated to dryness, crystallized from dry ether, centrifuged, washed with dry ether several times and dried. Thus 0.94 g of HCl.H-Arg(Mts)-OMe was obtained.

(2) $N^\alpha$-t-butoxycarbonyl-β-benzyl-L-seryl-$N^\omega$-mesitylenesulfonyl-L-arginine methyl ester [Boc-Ser(Bzl)-Arg(Mts)-OMe] (XII)

0.69 g (2.3 mmol) of Boc-Ser(Bzl)-OH and 0.94 g (2.3 mmol) of HCl-Arg(Mts)-OMe were dissolved in a mixture of 16.3 ml of purified DMF and 16.3 ml of dioxane and the obtained solution was stirred at 0° C. for 10 minutes. Then 0.76 ml (2.76 mmol) of DPPA and 0.74 ml (7.36 mmol) of TEA were added thereto and the mixture was stirred at room temperature for 24 hours. This solution was concentrated under reduced pressure and the dioxane was distilled off. An aqueous solution of NaCl was added to the residue and the precipitate thus formed was separated by decantation and washed with water. The residue was extracted with ethyl acetate and the extract was thoroughly washed with 5% citric acid, water and sodium bicarbonate, dehydrated over anhydrous sodium sulfate ($Na_2SO_4$), and concentrated to dryness.

(3) Boc.Gly-Ser(Bzl)-Arg(Mts)-OMe (XIII)

1.03 g of the compound (XII) was dissolved in 25.3 ml of dry dioxane and 25.3 ml of 4N HCl/dioxane was added thereto. The obtained solution was stirred at room temperature for 1 hour and then concentrated to dryness. It was then crystallized by adding dry ether and the crystals were centrifuged, washed with dry ether several times and dried. Thus 0.68 g (1.2 mmol) of HCl.H-Ser(Bzl)-Arg(Mts)-OMe was obtained. This compound was dissolved in a mixed solvent of 9.4 ml of purified DMF and 9.4 ml of dioxane, together with 0.26 g (1.5 mmol) of Boc-Gly-OH. After stirring at 0° C. for 10 minutes, 0.5 ml (1.8 mmol) of DPPA and 0.49 ml (4.8 mmol) of triethylamine were added thereto and the obtained mixture was stirred at room temperature for 24 hours. The solution thus obtained was subsequently treated in the same manner as in the synthesis of compound (XII), i.e. the solution was concentrated under reduced pressure and an aqueous solution of NaCl was added thereto. The precipitate thus formed was washed and dried in order that acidic and alkaline materials would be removed. Thus 0.48 g of Boc-Gly-Ser(Bzl)-Arg(Mts)-OMe was obtained.

(4) Boc-Gly-Ser(Bzl)-Arg(Mts)-OMe (XIV)

The Boc group of product (XIII) was removed by the same method as described in regard to compound (XI) to give 0.40 g (0.63 mmol) of HCl.H-Gly-Ser(Bzl)-Arg(Mts)-OMe. It was then dissolved in a mixed solvent of 5.4 ml of rectified DMF and 5.4 ml of dioxane together with the equimolar amount (0.14 g) of Boc-Ile-OH. The resulting solution was stirred at 0° C. for 10 minutes and then 0.21 ml of DPPA and 0.20 ml of triethylamine were added. The mixture was stirred at room temperature for 24 hours. The solution thus obtained was freed from any acidic and alkaline materials in the same manner as described in regard to compounds (XII) and (XIII). After drying, 0.28 g of Boc-Ile-Gly-Ser(Bzl)-Arg(Mts)-OMe was obtained.

(5) Boc-Tyr(Bzl)-Ile-Gly-Ser(Bzl)-Arg(Mts)-OMe (XV)

The Boc group of the product (XIV) was removed in the same manner as described in (1), except that approximately 2 or 3 times as much solvent was employed and the reaction time was extended to approximately 2 to 3 times in consideration of the length of the peptide chain and the steric hindrance of the Ile side chain. Namely, 0.28 g of the product (XIV), 6.0 ml of dry dioxane and 6.0 ml of 4N HCl/dioxane were employed while stirring was being conducted for a period of 2 hours. The resultant peptide [HCl.H-Ile-Gly-Ser(Bzl)-Arg(Mts)-OMe, yield: 0.14 g (0.19 mmol)] was dissolved in a mixture of 2.8 ml of rectified DMF and 2.8 ml of dioxane, together with 0.14 g (0.19 mmol) of Boc-Tyr(Bzl)-OH. The solution was stirred at 0° C. for 10 minutes. Next, 0.12 ml of DPPA and 0.72 ml of triethylamine were added thereto and the mixture was stirred at room temperature for 24 hours. The solution thus obtained was washed and dried, in the same manner as described regarding compound (XII). Thus 0.12 g of Boc- Tyr(Bzl)-Ile-Gly-Ser(Bzl)-Arg(Mts)-OMe was obtained.

(6) 0.14 g (0.13 mmol) of the product (XV) was dissolved in 1.95 ml of dry dioxane and 0.65 ml of 1N NaOH was added thereto. The mixture was stirred at room temperature for 3 hours. After removing the dioxane by concentrating under reduced pressure, approximately 20 ml of water was added and a small amount of insoluble matter was filtered off. The filtrate was cooled and 10% citric acid at 0° C. was added thereto. The precipitate thus formed was filtered, washed with a small amount of water twice and then dried. Thus 0.10 g of Boc-Tyr(Bzl)-Ile-Gly-Ser(Bzl)-Arg(Mts)-OH was obtained. This product was stirred in 6.0 ml of dry dioxane and 6.0 ml of 4N HCl/dioxane for 3 hours to remove the Boc group. Thus 0.08 g of HCl.H-Tyr(Bzl)-Ile-Gly-Ser(Bzl)-Arg(Mts)-OH was obtained.

(7) Poly(Tyr-Ile-Gly-Ser-Arg)HCl (XVII)

60 mg (0.061 mmol) of HCl.H-Tyr(Bzl)-Ile-Gly-Ser(Bzl)-Arg(Mts)-OH was dissolved in 0.2 ml of rectified DMSO and 0.07 ml of DPPA and 0.06 ml of triethylamine were added thereto. The solution was stirred at 0° C. for 1 hour followed by stirring at room temperature for 48 hours. After 48 hours, additional amount of DPPA and triethylamine, each in the same quantity as specified above, were added thereto and the mixture was stirred at 0° C. for 1 hour followed by stirring at room temperature for 48 hours. Water was added to the solution thus obtained and the mixture was centrifuged several times to remove the DPPA etc. After adding a small amount of methanol, centrifuge was repeated four more times to remove low molecular weight peptides dissolved in the methanol. Then the residue was centrifuged again by being dispersed in ether and dried. In order to remove the protecting groups in the side chains, a 40 mg portion of the resulting Poly(Tyr(Bzl)-Ile-Gly-Ser(Bzl)-Arg(Mts)) was added to a solvent mixture comprising 2 ml of trifluoroacetic acid and 0.4 ml of trifluoromethanesulfonic acid, together with 1 ml of thioanisole which was used as a scavenger. The mixture was stirred at 0° C. for 2 hours. The resulting solution was concentrated to dryness and dry ether was added thereto. The precipitate thus formed was washed with ether 4 times and dried. It was next dissolved in a small amount of water and passed through a column of an anion exchange resin (Amberlite IRA-400, Cl-form). The fraction containing the target product was concentrated to dryness and the residue was precipitated with a small amount of methanol. After washing with ether several times and drying, 22 mg of Poly(Tyr-Ile-Gly-Ser-Arg)HCl was obtained. This polypeptide had a molecular weight of approximately 10,000.

As described above, the novel polypeptide compound of the present invention having the repeated structure has a higher cell-adhesiveness, various biological activities including an antimetastatic effect, and scarcely any toxicity, as compared with the core sequences of cell-adhesive proteins. Furthermore, the polypeptide compound of the present invention has a relatively simple structure, which makes the synthesis thereof easy. Thus it is highly valuable as a drug.

What is claimed is:

1. A polypeptide of the following formula:

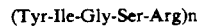

(Tyr-Ile-Gly-Ser-Arg)n wherein n is a number from 2 to 20 or a pharmaceutically acceptable salt thereof.

2. A pharmaceutical composition which comprises a pharmacologically effective amount of a polypeptide of the following formula:

(Tyr-Ile-Gly-Ser-Arg)n wherein n is a number from 2 to 20, or a pharmaceutically acceptable salt thereof, as an active ingredient, together with a pharmaceutically acceptable carrier.

3. A pharmaceutical composition according to claim 2, wherein said polypeptide has a molecular weight of approximately 10,000.

4. A polypeptide or a pharmaceutically acceptable salt thereof according to claim 1, having a molecular weight of approximately 10,000.

* * * * *